United States Patent
Boven et al.

(10) Patent No.: US 6,815,197 B2
(45) Date of Patent: Nov. 9, 2004

(54) APPARATUS FOR CONDUCTING ELECTROPHYSIOLOGICAL MEASUREMENTS ON CELLS

(75) Inventors: Karl-Heinz Boven, Kirchentellinsfurt (DE); Andreas Möller, Tübingen (DE)

(73) Assignee: Multi Channel System MCS GmbH, Reutlingen (DE)

(*) Notice: Subject to any disclaimer, the term of this patent is extended or adjusted under 35 U.S.C. 154(b) by 0 days.

(21) Appl. No.: 09/785,559

(22) Filed: Feb. 16, 2001

(65) Prior Publication Data

US 2002/0115196 A1 Aug. 22, 2002

(51) Int. Cl.[7] .............................. C12M 1/34; C12M 3/00
(52) U.S. Cl. ................ 435/285.1; 435/285.2; 435/287.1; 435/286.2; 435/288.4
(58) Field of Search ............... 435/285.1, 285.2, 435/286.2–286.5, 287.1, 287.3, 287.2, 288.4, 288.7; 600/345; 436/63

(56) References Cited

U.S. PATENT DOCUMENTS

| | | | |
|---|---|---|---|
| 4,128,456 A | * | 12/1978 | Lee et al. ............ 435/287.1 |
| 4,270,838 A | * | 6/1981 | Furusawa et al. ....... 359/385 |
| 5,462,645 A | | 10/1995 | Albery et al. |
| 5,888,825 A | * | 3/1999 | Carr et al. ............ 436/48 |
| 6,048,722 A | * | 4/2000 | Farb et al. ............ 435/287.1 |
| 6,063,260 A | | 5/2000 | Olesen et al. |
| 6,277,559 B2 | * | 8/2001 | Takeshita et al. ....... 435/4 |
| 6,461,860 B2 | * | 10/2002 | Mathes et al. ......... 435/286.7 |

FOREIGN PATENT DOCUMENTS

| | | | | |
|---|---|---|---|---|
| DE | 3134964 A | * | 3/1983 | ...... A61B/19/00 |
| GB | 2 297 383 | | 7/1996 | |
| JP | 11 083 785 | | 3/1999 | |
| JP | 11299496 A | * | 11/1999 | ...... C12Q/1/02 |
| WO | WO 9850791 A1 | * | 11/1998 | ...... G01N/33/483 |
| WO | WO 200034776 A1 | * | 6/2000 | ...... C12M/00/00 |

OTHER PUBLICATIONS

Costa, Alberto C. S. et al. "Improved technique for studtiny ion channels expressed in xenopus oocytes, including fast superfusion," BIOPHYSICAL JOURNAL, vol. 67, Jul. 1994, pp. 395–401.

* cited by examiner

Primary Examiner—William H. Beisner
(74) Attorney, Agent, or Firm—Weingarten, Schurgin, Gagnebin & Lebovici LLP

(57) ABSTRACT

Apparatus for conducting electrophysiological measurements on cells wherein a measuring head is provided with at least one electrode in a common support for impaling the cells.

54 Claims, 3 Drawing Sheets

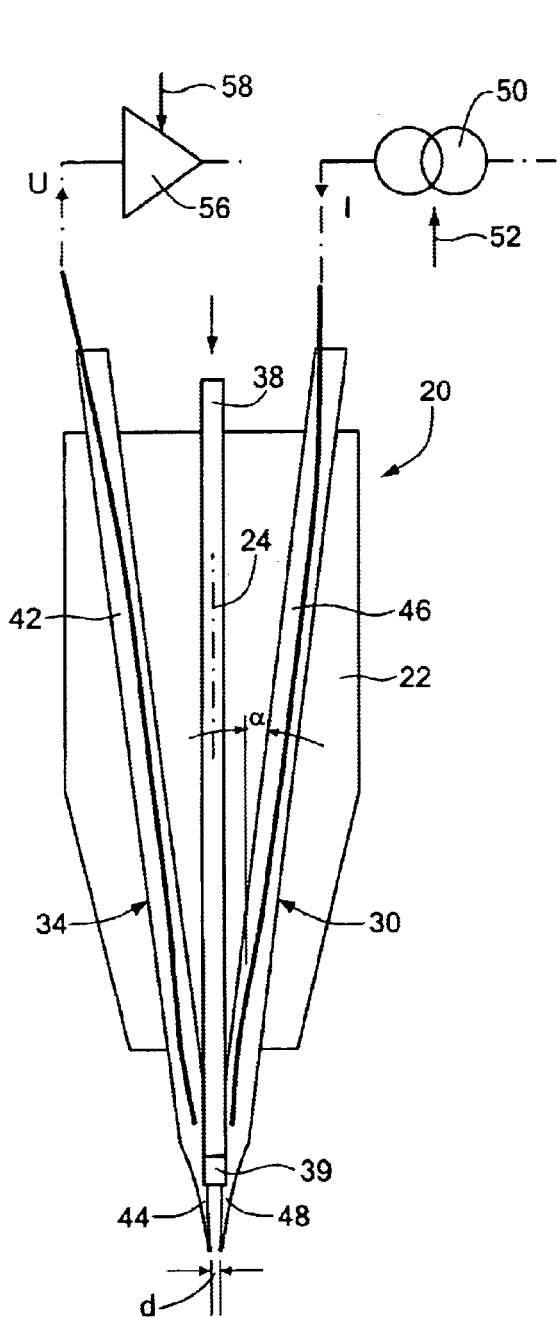
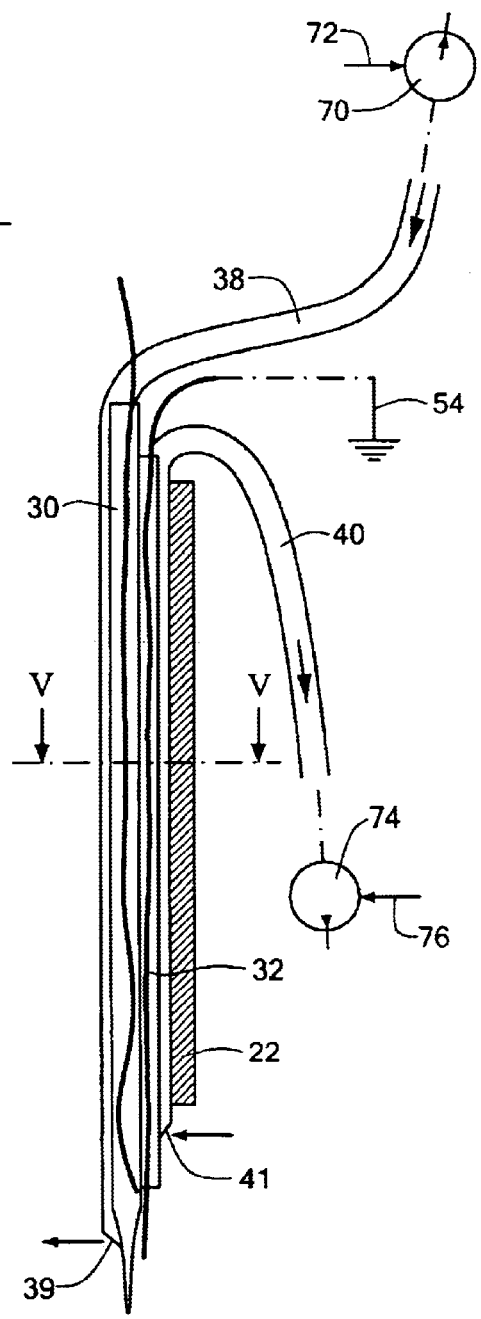
*FIG. 3*          *FIG. 4*

APPARATUS FOR CONDUCTING ELECTROPHYSIOLOGICAL MEASUREMENTS ON CELLS

The invention is related to an apparatus for conducting electrophysiological measurements on cells comprising a measuring head, the measuring head being provided with at least one electrode for impaling the cells.

An apparatus of the afore-mentioned type is disclosed in U.S. Pat. No. 6,048,722.

The prior art apparatus is used for conducting electrophysiological measurements on oocytes, in particular oocytes of Xenopus laevis, a South African claw frog. These oocytes are preferably used as expression systems for electrophysiological measurements. For that purpose the oocyte is placed and immobilized in a receptacle. The receptacle may, for example, be a funnel-type opening within a plate. Such plates are standardized and are conventionally used with 8×12=96, 16×24=384 or 32×48=1.536 receptacles ("wells"). The receptacles for the oocytes may, for example, be provided with an opening at their bottom side, enabling to attract the oocyte by means of vacuum and to immobilize same within the receptacle.

For conducting electrophysiological measurements a genetic information, namely a mRNA or a cDNA is injected into the oocyte. As a consequence, characteristic ion channels and/or receptors are incorporated on the surface and within the oocyte which may be measured by applying an electrical voltage or directing an electrical current therethrough or by application of a substance.

It is well known to conduct pharmacological measurements in this manner because the receptors or ion channels developed in the membrane of the oocytes are configured in a kind that is characteristic for certain properties of the substances under investigation.

Within the apparatus according to U.S. Pat. No. 6,048,722 mentioned at the outset, a measuring electrode and a reference electrode are impaled into the cell. In addition a perfusion apparatus is connected to the receptacle of the cell. By means of this perfusion apparatus various substances, in particular measuring substances, may be filled into the receptacle in a controlled manner, the receptacle having typically a volume of 100 $\mu$l.

Although this prior art apparatus is automatized for what concerns the supply of perfusion agents, it requires a considerable manual talent to bring the perfusion conduit into the area of the receptacle for the cell and to immobilize same at that location. Above all, the application of the electrodes to the cells, in particular impaling the electrodes into the cell, depends on the manual skill of the particular person conducting the experiment because these steps obviously have to be made manually. In case the application of the electrode or electrodes to the cell is unsuccessful, in particular, if the electrodes brake off, the entire experimental set up must be wholly re-assembled and re-adjusted. Finally, the prior art apparatus only allows to conduct individual measurements on one cell wherein only the sequence of different test fluids may be controlled automatically in a manner mentioned above.

It is, therefore, an object underlying the invention to improve an apparatus of the type specified at the outset such that the above-discussed disadvantages are avoided.

In particular it shall become possible to fully automatically conduct the experiments as well with respect to application of the electrodes as well as with respect to the application of the perfusion conduits. Further, the apparatus shall be adapted to be made ready for use with only a couple of manual operations according to the "plug-and play" principle and it shall be possible with the same principle that the apparatus can be put back to operation after a damage has happened.

Finally it shall become possible to execute a plurality of measurements on many different cells in a fully automatized mode, i.e. without supervision, in particular over night.

According to the apparatus specified at the outset this object is achieved by the present invention in that the electrodes are integrated into a common support.

This measure has the advantage that the carrier may be prefabricated on an industrial level and must, hence, only be plugged on a corresponding holder within the apparatus. The electrodes are already installed ready for operation, in particular with respect to their position relative to one another so that in contrast to conventional apparatuses there is no more need to delicately adjusting and orienting the electrodes relative to one another. By doing so the risk of damaging the electrodes during the setup of the apparatus is drastically minimized. Further, the measurements are clearly reproducible, because the electrodes are in a predetermined position relative to one another. Finally the integrated arrangement of the electrodes on the support allows that automatic displacement units for the measuring head thus obtained may be made, enabling to conduct the desired fully automatic measurements on a plurality of cells, for example in connection with a standardized multiwell-plate.

In preferred embodiments of the inventive apparatus the electrodes are inserted into recesses of the carrier, however, they may also be molded within the carrier.

This measure has the advantage that a stable and reproducible position of the electrodes within the carrier is achieved.

In other embodiments of the invention the electrodes consist of pulled glass tubes.

This measurement has the advantage that such glass electrodes may be configured optimally for the specific application, as known per se. For example, it is possible to configurate the electrodes to have an electrical resistance of between 5 M$\Omega$ and 100 M$\Omega$, i.e. as so-called "sharp electrodes". As an alternative, the electrodes may be configurated as so-called "patch electrodes" having an electrical resistance of the order of 500 k$\Omega$ through 5 M$\Omega$.

As an alternative, the invention may provide to configurate the electrodes as wire electrodes, preferably as silver wire electrodes which, further preferably, are surrounded by a chloride coating. Besides that also tungsten wires or the like may be used.

In preferred embodiments of the inventive apparatus at least one electrode is provided with a straight section.

This measure has the advantage that the electrode may particularly easily be attached to the support.

In another preferred embodiment of the invention two electrodes are arranged essentially symmetrical relative to a longitudinal axis of the carrier so that the distance between the free ends of the electrodes are in a range of between about 50 $\mu$m and 800 $\mu$pm, preferably between 200 $\mu$m and 500 $\mu$m.

This measure has the advantage that during the introduction of the electrodes into the cells individual impaling holes are generated and not a common big hole which would be the case if the free ends of the electrodes would be arranged too close to one another. This would have the disadvantage that important physiological functions of the cells would go lost. With the inventive approach this is avoided.

In this connection it is particularly preferred when a straight section of the electrodes encloses an acute angle with a longitudinal axis of the support, the angle being in particular between 3° and 10°, preferably 5°.

The inclined orientation of the electrodes with respect to one another has the advantage that the lower free ends of the electrodes may be positioned in a perfectly reproducible manner.

In a preferred group of embodiments of the invention at least one electrode is configured as a measuring electrode. The measuring electrode is preferably connected to a measuring amplifier which, further preferably, is adapted to be adjusted.

By doing so it is possible to conduct automatically con-trolled measurements of voltage and current signals.

This holds true in particular if the at least one measuring electrode is connected to a current source and the current source, in turn, is adapted to be adjusted.

This measure has the-advantage that if two different electrodes are used, the feeding of current on the one hand and the measuring of voltage on the other hand are decoupled one from the other.

The currents and voltages to be measured in the present context are in the nA through µA range for currents and in the mV range for voltage measurements.

These measurements may be conducted by conventional electrophysiological measuring methods like "bridge-mode", "currentclamp", and "voltage-clamp". In so far it is irrelevant for the invention whether the voltage clamp derivation is executed with two electrodes (two-electrode voltage clamp; TEVC) or with one electrode (single-electrode voltage-clamp, SEVC). In the SEVC method measurements are made in the so-called "switched-mode", i.e. within a predetermined interval a measuring current is injected and the measuring voltage (with the current injection switched off) is alternately measured.

For that purpose it is preferred with further embodiments to at least configurate one of the electrodes as a reference electrode. In that case the reference electrode is preferably connected to ground.

In that case it is particularly preferred if at least two measuring electrodes are located in a first common plane and/or at least two reference electrodes are located in a second common plane and, further preferably, the first and the second plane extend parallel to each other and have a distance from each other which is as small as possible.

These measures have the advantage that an extremely compact design is achieved that is optimized from the point of view of the measuring technology and in which all necessary components are integrated as densely as possible.

In a further group of embodiments at least one perfusion conduit is arranged on the support.

This measure has the advantage that the perfusion apparatus is integrated into the same measuring head with respect to the feeding and discharging of the perfusion agent, the measuring head being the same in which the electrodes are already located so that all these elements may be handled altogether. Another advantage is that during the integration also of the perfusion conduits into the measuring head the relative positioning of the perfusion conduits relative to the electrodes may be optimized and may already be fixed in the manufacturing site. Also insofar a cumbersome handling of the apparatus during the setup of the measuring equipment has become obsolete. Further, one has the advantage that if one of the components should be damaged the entire measuring head may be replaced by another one with only a couple of manual operations.

According to variations of this group of embodiments the at least one perfusion conduit may be a perfusion inlet.

In that case it is particularly preferred when the perfusion inlet has a first end opening, when the perfusion inlet is arranged essentially parallel to the at least one electrode and if, finally, the first end opening is arranged above a lower end of the at least one measuring electrode.

This measure has the advantage that the perfusion agent is guided directly and exactly to the spot where the active portion of the measuring electrodes is located.

This holds true in particular if in connection with the already above-mentioned symmetrical arrangement of the electrodes the perfusion inlet is located essentially on the symmetry axis between the measuring electrodes.

It is, further, preferred in this context when the perfusion inlet is connected to a pump, the pump being preferably adapted to be adjusted.

This measure has the advantage that the perfusion agent may be supplied in precise quantities.

According to further variations of this embodiment the perfusion inlet is adapted to be connected to a plurality of storage containers via a controllable valve system, the containers containing a test fluid or a rinsing fluid.

This measure has the advantage that with respect to the perfusion apparatus fully automatic measurements may be conducted with the already mentioned advantages.

It is particularly preferred when the storage container is arranged above the perfusion inlet.

In that case a pump is, namely, not necessary because after opening a valve in a respective connecting conduit the test or rinsing liquid may flow to the perfusion inlet under the action of gravity alone.

In another group of embodiments the perfusion conduit is a perfusion outlet.

This measure has the advantage that the perfusion agent that is no more required may be disposed off in a controlled manner so that in particular a spill over in the receptacle for the cell is avoided.

For that purpose the perfusion outlet is preferably provided with a second end opening being located above the first end opening.

This measure has the advantage that the cell is continuously supplied with fresh perfusion agent via the distance between the two end openings, i.e. either with a test liquid or with a rinsing liquid between the measuring steps.

Moreover, this measure has the advantage that also outside the measuring operations as such the perfusion agent may be supplied in a controlled manner in order to protect those cells that are not subjected to measurements against becoming dried out. In that case a predetermined level of liquid above the cells may be set by appropriately setting the vertical distance between the two end openings.

A particularly good effect is achieved when the two openings are oriented in opposite directions.

This measure has the advantage that a short circuit between the inlet and the outlet system is avoided because the inlet and the outlet are effected in opposite directions.

Also in that case it is likewise preferred when the perfusion outlet is connected to a suction pump, particularly an adjustable pump.

A particularly good effect is achieved when, as viewed in the direction on to the first plane, the perfusion inlet is arranged in front of the first plane and the perfusion outlet is arranged behind the second plane. This measure has the advantage that an extremely compact and safe assembly is generated in which all components necessary for the measurements may cooperate in an optimal way.

In embodiments of the invention it is preferred when at least one measuring head is arranged on an actuator and the actuator is adapted to be displaced along a coordinate system above the receptacles for the cells.

This measure has the advantage that the measuring head may be displaced along all directions of the coordinate system in a fully automatic manner so that all necessary movements may be effected under program control. This holds true in particular for impaling the cells by means of the measuring electrodes, however, also for approaching the measuring head to the cells, if only a moisturizing of the cells with perfusion agent is required, as was explained above.

In a preferred modification of this embodiment the actuator may carry a plurality of measuring heads.

This measure has the advantage, in particular when so-called multi-well-plates are used, that several cells may be measured along a row or a column of the plate in parallel and simultaneously so that the cells contained in the wells of the plate may be measured as a whole only in a fraction of the time that would be required otherwise. When doing so it is of course possible to operate with different perfusion agents within different receptacles for the cells, i.e. with different test liquids or with different rinsing liquids. If different test liquids are used, this may mean that the same type of test liquid is used, however, in different concentrations, however, also test liquids of entirely different kinds may be utilized.

In that case it is proper to make all measuring heads displaceable relative to the actuator at least along a direction directed to the cell.

This measure has the advantage that the movements relative to a cell may be individually set, even if several cells are measured in parallel as discussed above.

In a particularly preferred embodiment of the inventive apparatus the measuring head is adapted to be plugged or screwed onto the actuator.

This measure has the advantage that a quick replacement of the measuring head has become possible without the need of modifying the entire experimental setup.

In another preferred embodiment of the invention means are provided for injecting cDNA and/or mRNA into the cell. This is preferably effected by arranging such means on the actuator.

These measures have the advantage that also during the step of injecting (being known per se) this step is automatized in the discussed manner and, as the case may be, may be effected for a plurality of cells one after the other in a controlled fashion.

It has already been mentioned that the invention in a highly preferred way may be utilized when the receptacles for the cells are configured as a standardized multi-well-plate.

In that case a particularly good effect is achieved if the individual receptacles in the plate are provided with a readable code, and the actuator comprises means for reading the code. This holds true in particular when the code is a bar code and means are configured as a bar code reading head.

This measure has the advantage that the inventive apparatus may start its measurements at a certain predetermined cell in a predetermined well at the beginning of the automatized measuring process for a plurality of cells, and may then continue its way over the multi-well-plate according to the particular program. At each individual receptacle, in particular at each individual well it is possible to check, by reading the respective bar code, whether the position of the measuring head is correct.

Further advantages will become apparent from the description and the enclosed drawing.

It goes without saying that the advantages mentioned before and those that will be explained hereinafter may not only be used in the particularly given combination, but also in other combinations or alone, without leaving the scope of the present invention.

Embodiments of the invention are shown in the drawings and will be explained throughout the subsequent description. In the drawing:

FIG. 3 is a front elevational view, on an enlarged scale, showing a measuring head as may be used in the apparatus of FIG. 2;

FIG. 4 is a side elevational view, partially cut away, through the measuring head of FIG. 3;

Figure 1:
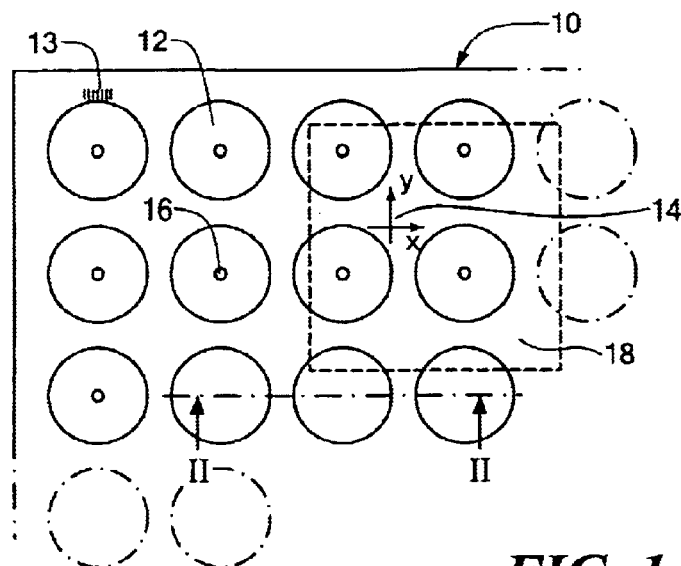
FIG. 1 is a top plan view on one portion of a multi-well-plate as it may be advantageously used within the scope of the present invention.

In FIG. 1, reference numeral 10 as a whole indicates a so-called well-plate as is used during electrophysiological measurements on oocytes. Well-plates 10 are standardized and comprise a plurality of wells 12, i.e. receptacles for Oocytes. Standardized well-plates 10 are provided with wells 12 in rows and columns. Conventionally, formats of 8×12=96, 16×24=384 or 32×48=1.536 wells are used.

For locating and identifying individual wells 10, codes are applied, one of which being indicated at reference numeral 13 as a bar code.

The rows and columns of wells 12 within well-plate 10 define a coordinate system 14. In standardized well-plates 10 a cartesian coordinate system having axes x and y is used.

In FIG. 1 one oocyte each is indicated within wells 12 at reference numeral 16. During electrophysiological measurements of the kind of interest in the present context oocytes of the South African claw frog (Xenopus laevis) are conventionally used. These oocytes 16 have a diameter of approximately 1 mm. As becomes apparent from the cross sectional view of FIG. 2, wells 12 have a convex shape which, preferably, narrows in a downward direction.

In order to immobilize oocytes 16 within wells 12, means may be provided for connecting wells 12 at their lowermost point to a channel of a vacuum system (not shown in the drawing), in order to immobilize oocytes 16 within wells 12 via vacuum.

Figure 2:
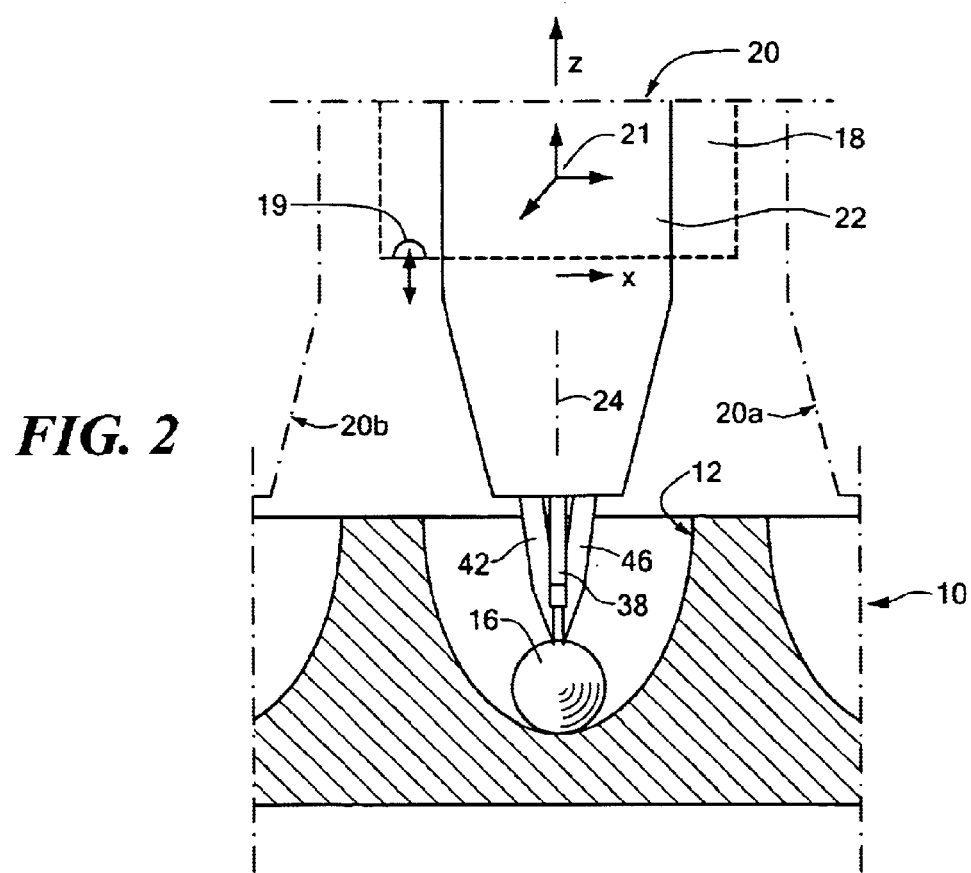
FIG. 2 is a side elevational view, partially cut away, along line II—II of FIG. 1, of an embodiment of an apparatus according to the invention.

In FIGS. 1 and 2 an actuator is indicated at reference numeral 18. Actuator 18 is adapted to be displaced along planar coordinates x and y, however, also along coordinate z being perpendicular thereto. For that purpose, actuator 18 is connected to an electronic control unit (not shown) providing the required control signals to corresponding displacement units for the three coordinates x, y and z. The capability of actuator 18 to be displaced along three dimensions is also indicated in FIG. 2 at reference numeral 21.

Actuator 18 is provided with a reading head 19 at its lower side. Reading head 18 is configured as a bar code reader, for example.

Reading head 19 is capable of identifying all codes 13 at each well 12 so that each well 12 maybe identified with its coordinates on well-plate 10.

Actuator 18 carries a measuring head 20 for conducting measurements on oocytes 16 as will be described below.

Measuring head 20 comprises a support 22 into which all elements are integrated that are required for measuring purposes, as will be explained in detail below together with FIGS. 3 through 5. Support 22 has a longitudinal axis 24 which, in the shown embodiment, coincides with the vertical z-axis.

Reference numerals 20a and 20b, further, indicate in FIG. 2 that not only one measuring head 20 but instead several measuring heads 20, 20a, 20b . . . may be provided above well-plate 10. Preferably, measuring heads 20, 20a, 20b are arranged in a row so that a plurality of oocytes 16 within wells 12 may be measured simultaneously. This may apply for an entire row or column of wells 12 within the well-plates, for example.

Preferably the entire row of measuring heads 20, 20a, 20b is displaced together above well-plate 10 in order to be subsequently targeted towards various rows or columns, respectively, of wells 12, however, it is preferred that at least the z-drive of any actuator 18 for each individual measuring head 20, 20a, 20b . . . remains to be controlled individually in order to enable the measuring on each individual oocyte 16 as such individually after having arrived at the particular well 12.

Figure 5:
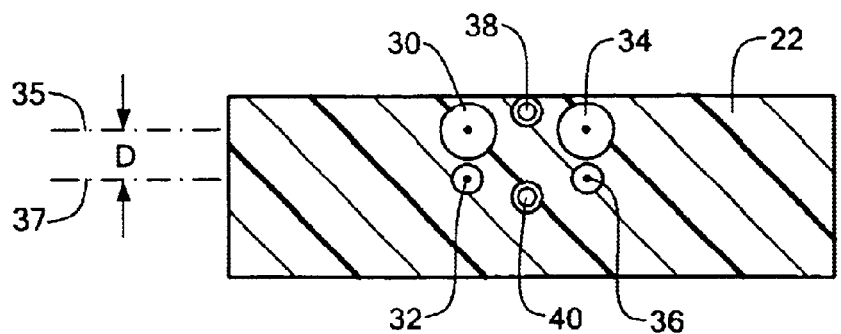
FIG. 5 is a cross-sectional view along line V—V in FIG. 4, on a further enlarged scale, for explaining further details of the illustrated measuring head.

In FIGS. 3 through 5 measuring head 20 is shown in further detail.

Each measuring head 20 is provided with a first electrode 30, a first reference electrode 32, a second electrode 34 as well as a second reference electrode 36.

As may be seen from the enlarged scale cross-sectional view according to FIG. 5, electrodes 30 and 34 are arranged in a common first plane 35, whereas reference electrodes 32 and 36 are arranged within a second plane 37. Planes 35 and 37 extend parallel to one another and have a distance D from each other.

Support 22, further, houses a perfusion inlet 38 having a lower end opening 39 and a perfusion outlet 40 having a lower end opening 41. As viewed from first plane 35, perfusion inlet 38 is located in front of first plane 35, whereas perfusion outlet 40 is located behind second plane 37. Perfusion inlet 38 and perfusion outlet 40 lie in the center median plane between electrodes 30, 34 and reference electrodes 32 and 36. The center median plane coincides with the longitudinal axis 24 of support 22.

Electrodes 30 and 34 each have a straight section 42 and 46, respectively, and terminate at their lower end in tips 44 and 48, respectively. Straight sections 42, 46 are inclined relative to longitudinal axis 24 of support 22, the angle α of inclination being, preferably, between 3° and 10°, in particular 5°.

The arrangement was selected such that tips 44 and 48 have a very small distance d from each other, distance d being between 200 μm and 500 μm. In contrast, distance D between planes 35 and 37 is of the order of 1 mm.

Reference electrodes 32 and 36 in FIG. 3 lie behind measuring electrodes 30, 34 and are likewise arranged in an inclined fashion.

As has already been mentioned, electrodes 30 and 34 are intended to be used as measuring and as derivation electrodes. They can be configured as so-called glass electrodes being manufactured from pulled glass tubes. In the terminology of electrophysiology these electrodes are designated as "sharp electrodes" if they have an electric resistance of the order of between 5 and 100 MΩ, or as "patch electrodes" if their electrical resistance is of the order of between 500 kΩ and 5 MΩ. In practice the so-called "patch electrodes" are used for impaling as well as for sucking. As an alternative, electrodes made from wire may be used which may consist of tungsten, for example, and which are conventionally designated as "wire electrodes".

In contrast, reference electrodes 32 and 36 are preferably configured as wire electrodes. For that purpose silver wires may be used being covered with a chloride coating obtained through electrolytic processes. Such electrodes are designated as Ag/AgCl-electrodes.

The perfusion conduits 38 and 40 are configured as hoses.

The six afore-mentioned elements 30, 32, 34, 36, 38 and 40 are integrated into support 22 of measuring head 20 as shown in FIG. 5. The term "integrated" is to be understood to comprise various kinds of application. For example, the elements may be inserted into corresponding bores, recesses, milled-out areas or the like within the one-piece carrier body or may be affixed thereto otherwise. However, it is also possible to embed the afore-mentioned elements altogether into carrier 22 by molding. The important thing is that all afore-mentioned elements i.e. all elements and perfusion conduits are immobilized within carrier 22 with respect to their position and dimension so that they may easily be put in place as "plug-and-play" units or may eventually be exchanged. For that purpose carrier 22 should be plugged to measuring head 20 or be otherwise connected in a releasable manner.

FIGS. 3 and 4 show the corresponding circuitry for the aforementioned elements.

It may be seen that first measuring electrode 30 is connected to a current source 50 being adjustable via a control terminal 52. Current source 50 supplies a current I for first measuring electrode 30.

Second measuring electrode 34, in contrast, is connected to a measuring amplifier 56 having a control input 58. Measuring amplifier 56 amplifies and/or otherwise processes a voltage signal U detected by second measuring electrode 34.

Perfusion inlet 38 is connected to a conveyor pump 70 which, in turn, has a control input 72. Pump 70, via a corresponding valve system, may be connected to a plurality of storage containers having various measuring or rinsing agents contained therein.

In contrast, perfusion outlet 40 is connected to a suction pump 74 having a control input 76.

The inventive apparatus, further, is provided with elements permitting to inject cDNA and/or mRNA into the oocytes 16 to be measured. The components required therefore are also preferably coupled to actuator 18 so that they, too, may be driven to each individual oocyte 16 within each predetermined well 12.

When using the afore-explained apparatus the following measurements may be conducted:

First, oocytes 16 are brought into the, for example, 96 wells 12 of well-plate 10. Oocytes 16 are then provided with cDNA or mRNA by injecting these substances into oocytes 16, either sequentially or simultaneously in groups. The oocytes are then incubated, for example for a period of time of two or more days.

For performing the subsequent measurements, actuator 18 is first displaced along coordinate system 14, i.e. along the x- and the y-direction above well-plate 10, until it has come to a predetermined well 12 as detected by reading the corresponding bar code 13.

In that position measuring head 20 is lowered by displacing same along the z-axis until tips 44, 48 are located above oocyte 16.

The apparatus is now first operated in the "current clamp" mode by keeping the current constant within the nA through the μA range. This is effected by adjusting current source 50 via control input 52. Current source 50 insofar is assumed to be an ideal current source so that a current I once set is subsequently automatically held constant.

Due to the relatively low resistance at that moment in time a relatively low measuring voltage U will develop at measuring electrode 34 which is detected within amplifier 56.

Measuring head 20 is then further lowered along the z-direction until tips 44, 48 penetrate into oocyte 16. Due to the penetration two holes are generated within oocyte 16 being spaced by distance d.

Due to the sudden rise of the electrical resistance a substantial voltage rise occurs in measuring voltage U.

The apparatus is now switched from the "current clamp" mode into the "voltage clamp" mode. In that mode of operation voltage U within measuring amplifier 56 is held constant by correspondingly controlling current I via adjustable current source 50.

At that moment in time pump 70 is connected to a storage container having a substance under test therein, or the substance under test flows to perfusion inlet 38 under the action of gravity. Pump 70 is now switched on via control input 72 (and/or a corresponding valve within the supply line for perfusion inlet 38 is opened), so that a substance under test may flow as shown by arrows in FIG. 4. The substance under test will now flow through perfusion inlet 38 and out of end opening 39. End opening 39 is so oriented that the substance under test will flow away in a horizontal direction to the left hand side in FIG. 4. Simultaneously suction pump 74 is switched on so that exceeding substance under test will be sucked away via opening 41 and perfusion outlet 40. Opening 41, too, is horizontally oriented, however, in a direction opposite to that of opening 39. As a consequence, a short-circuit between openings 39 and 41 is effectively avoided.

Seen as a whole, the result is that the substance under test covers oocyte 16 at a predetermined level being determined by the vertical distance of openings 39 and 41 with respect to each other.

By applying the substance under test oocyte 16 opens its ion channels.

Accordingly, variations in current within the nA through the μA range are generated, these variations being measured via measuring amplifier 56 and are subsequently recorded.

Figure 6:
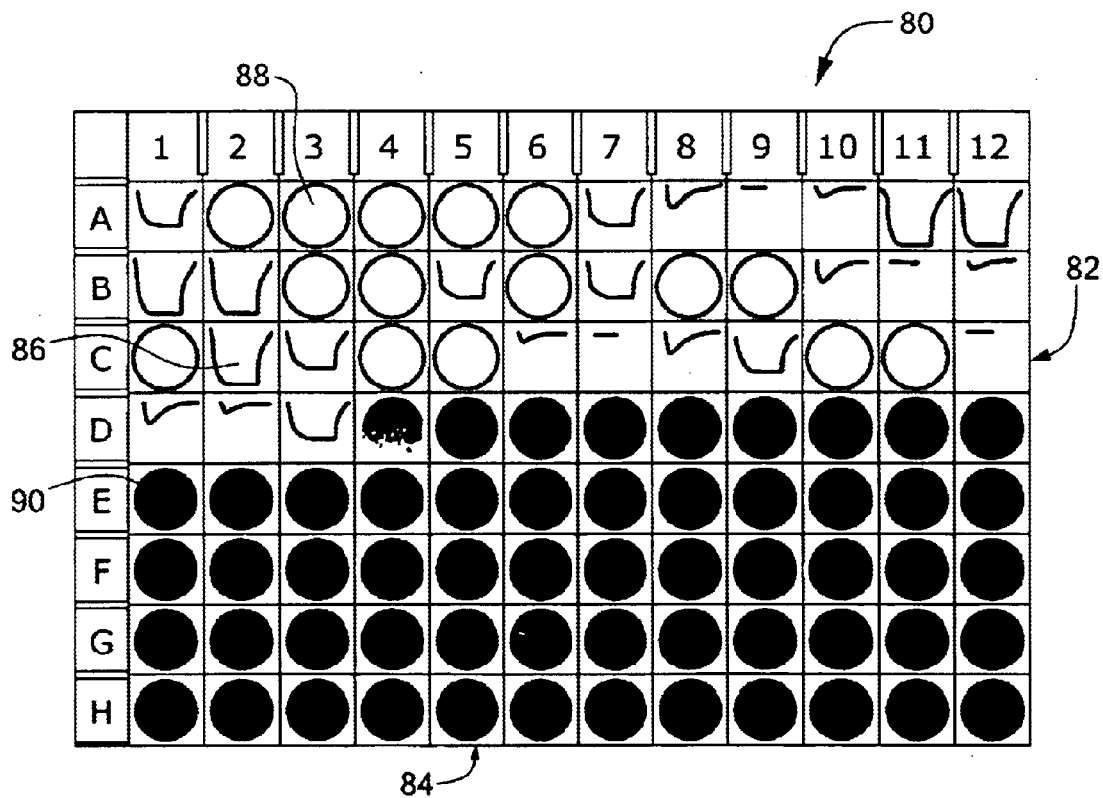
FIG. 6 is a printout of a measurement as may be executed with the apparatus according to FIGS. 2 through 5.

FIG. 6 shows a corresponding measurement printout or protocol 80. Measurement protocol 80 is subdivided into rows 82 and columns 84 corresponding to the distribution of wells 12 within well-plate 10. In the example shown measurement protocol 80 for a 96-well-plate comprises rows 82 with twelve positions 1 through 12 as well as columns 84 with eight positions A through H.

In FIG. 6 a first field having the coordinates C2 is designated by reference numeral 86, a second field having the coordinates A3 by 88 and a third field having the coordinates E1 by 90.

Within the first field 86 one may see how the current develops prior to and during the application of the test substance, corresponding to a successful measurement on oocyte 16 located within well 12 at coordinate position C2.

Second field 88, in contrast, designates an unsuccessful measurement as symbolized by a circle.

Measurement protocol 80 shows a situation in which wells 12 have been processed up to coordinate position D4. All subsequent wells 12 have not been processed as yet as indicated, for example, by a circular dot within third field 90.

The user of the apparatus may, hence, determine by simply having a look at measurement protocol 80, in which wells the measurements have been successful, in which wells the measurements have been unsuccessful and which wells have not yet been examined.

If for a specific well 12 the measurement is terminated, measuring head 20 is again lifted in the z-direction and a connection may now be made to another storage container by appropriately switching the input pump 70. The other storage container may contain a rinsing agent and that rinsing agent is then fed to well 12. The rinsing agent is now circulated by feeding same through perfusion inlet 38 and subsequently sucking it away somewhat above perfusion outlet 40, until, finally, oocyte 16 has been entirely rinsed and all traces of the measuring substance having been applied before are removed.

Another measurement may then be conducted by feeding another measuring agent in the same manner as already described. The other measuring agent may be the same measuring agent as before, however, in another concentration, however, also entirely different measuring agents may be applied.

Further, it goes without saying that the afore-explained measuring and rinsing steps may all be effected in the same vertical position z of measuring head 20, depending on what seems to be appropriate in view of the particular circumstances of the given situation.

The inventive apparatus, however, may also be used to effect other functions other than the measurements as such:

Oocytes 16 within wells 12 are namely not subjected to measurements and, hence, not provided with test liquids over extended periods of time so that there is the risk that oocytes 16 will dry out over these extended intermissions. There is a substantial such risk during the conventional incubation time of two days after the initial injection of cDNA/mRNA. Further extended intermissions may occur between subsequent measurements if only one measuring head 20 is utilized and 96, 384 or even 1.536 wells 12 of standardized well-plates 10 are measured.

In order to avoid that oocytes 16 dry out during these extended intermissions, prior to the measurements as such or between two measurements, measuring head 20 may be displaced above the wells in question in a manner as already discussed in order to apply a moisturizing liquid onto oocytes 16 via perfusion system 38/40 in order to avoid that they dry out.

In the inventive apparatus measuring head 20 is assembled at the manufacturing site. This means that all individual components are mounted on measuring head 20 and are adjusted under microscopic control at the manufacturer's site. The measuring head 20 so assembled is then handed over to the user. The user may manually attach measuring head 20 at actuator 18 with a couple of manipulations or may replace same by another, if necessary. Measuring head 20 may immediately be mounted on the z-axis after derivation electrodes 30, 34 have been filled with corresponding conductive solutions. After having made all electrical connections and after having connected the perfusion system, the measuring operation may immediately be started. This "plug-and-play" capability of measuring head 20 is a substantial simplification for the user. In contrast to conventional apparatuses the user must not manufacture the electrodes by himself, adjust same, chloridize same and adapting reference electrodes. Finally, there is no need for attaching and positioning the perfusion conduits.

It goes without saying that the inventive apparatus of measuring head 20 may be provided with any arbitrary combinations of electrodes and perfusion conduits. However, it is particularly preferred in the present instance to use an assembly comprising a total of six elements, as shown in detail in FIG. 5.

Measuring head 20 is preferably used within automatic actuators or robotic systems, however, it may also be used in conventional manual systems, in particular in so-called micromanipulators.

What is claimed is:

1. An apparatus for conducting electrophysiological measurements on cells comprising a measuring head provided with at least one measuring electrode for impaling said cells, with at least one reference electrode, with at least one perfusion conduit made as a perfusion inlet having a first end opening, wherein said at least one measuring electrode and said at least one reference electrode are molded into a common support, said at least one perfusion inlet being arranged essentially parallel with said at least one measuring electrode, and said first end opening being located above a lower end of said at least one measuring electrode.

2. The apparatus of claim 1 wherein said at least one measuring electrode and said at least one reference electrode are inserted into recesses within said support.

3. The apparatus of claim 1 wherein said at least one measuring electrode and said at least one reference electrode consist of pulled glass tubes.

4. The apparatus of claim 1 wherein said at least one measuring electrode and said at least one reference electrode have an electrical resistance of between 5 MΩ and 100 MΩ.

5. The apparatus of claim 1 wherein said electrodes have an electrical resistance of between 500 kΩ and 5 MΩ.

6. The apparatus of claim 1 wherein said at least one measuring electrode and said at least one reference electrode are configured as wire electrodes.

7. The apparatus of claim 6 wherein said at least one measuring electrode and said at least one reference electrode are configured as silver wire electrodes.

8. The apparatus of claim 7 wherein said at least one measuring electrode and said at least one reference electrode are configured as silver wire electrodes provided with a chloride coating.

9. The apparatus of claim 1 wherein least one electrode has a straight section.

10. The apparatus of claim 1 wherein least one electrode is provided with a tip at its front terminal end.

11. The apparatus of claim 1 wherein two electrodes are arranged essentially symmetrical relative to a longitudinal axis of said support.

12. The apparatus of claim 11 wherein said electrodes have a distance d at their free terminal end being between 50 μm and 800 μm.

13. The apparatus of claim 12 wherein said distance d is between 200 μm and 500 μm.

14. The apparatus of claim 11 wherein at least one electrode has a straight section, said straight section enclosing an acute angle α with a longitudinal axis of said support.

15. The apparatus of claim 14 wherein said acute angle α is between 3° and 10°.

16. The apparatus of claim 15 wherein said acute angle α is 5°.

17. The apparatus of claim 1 wherein said at least one measuring electrode is coupled to a measuring amplifier.

18. The apparatus of claim 17 wherein said measuring amplifier is adapted to be adjusted.

19. The apparatus of claim 1 wherein said at least one measuring electrode is connected to a current source.

20. The apparatus of claim 19 wherein said current source is adapted to be adjusted.

21. The apparatus of claim 1 wherein said reference electrode is connected to ground.

22. The apparatus of claim 21 wherein two measuring electrodes and two reference electrodes are provided.

23. The apparatus of claim 22 wherein at least two reference electrodes are arranged in a second common plane.

24. The apparatus of claim 1 wherein at least two measuring electrodes are arranged in a first common plane.

25. The apparatus of claim 24 wherein said first and a second plane extend parallel to each other and wherein at least two reference electrodes are arranged in said second common plane.

26. The apparatus of claim 25 wherein, as viewed on first plane, said perfusion inlet is located in front of said first plane and a perfusion outlet is located behind said second plane and wherein at least one perfusion conduit is said perfusion outlet.

27. The apparatus of claim 1 wherein said perfusion inlet is arranged essentially on a symmetry axis between two measuring electrodes, said perfusion inlet being arranged essentially parallel with said two measuring electrodes said first end opening being located above a lower end of said two measuring electrodes.

28. The apparatus of claim 1 wherein said perfusion inlet is connected to a conveyor pump.

29. The apparatus of claim 28 wherein said pump is adapted to be adjusted.

30. The apparatus of claim 1 wherein said perfusion inlet is adapted to be connected to a plurality of storage containers via a controllable valve system.

31. The apparatus of claim 30 wherein said storage containers are arranged above said perfusion inlet.

32. The apparatus of claim 30 wherein said storage containers contain a test liquid.

33. The apparatus of claim 30 wherein said storage containers contain a rinsing liquid.

34. The apparatus of claim 1 wherein at least one perfusion conduit is a perfusion outlet.

35. The apparatus of claim 34 wherein said perfusion outlet has a second end opening said second end opening being located above the first end opening.

36. The apparatus of claim 35 wherein said end openings are oriented along opposite directions.

37. The apparatus of claim 34 wherein said perfusion outlet is connected to a suction pump.

38. The apparatus of claim 37 wherein said suction pump is adapted to be adjusted.

39. The apparatus of claim 1 further comprising a receptacle for said cells wherein said measuring head is arranged on an actuator, said actuator being adapted to be displaced long a coordinate system above said receptacle.

40. The apparatus of claim 39 wherein said actuator carries a plurality of measuring heads.

41. The apparatus of claim 40 wherein said measuring heads are adapted to be displaced individually relative to said actuator along said axis z directed towards said cell.

42. The apparatus of claim 39 wherein said measuring head is affixed to said actuator by plugging or screwing.

43. The apparatus of claim 39 wherein said receptacle for said cell is configured as a standardized multi-well-plate.

44. The apparatus of claim 43 wherein individual wells within said plate are provided with a readable code, said actuator comprising means for reading said code.

45. The apparatus of claim 44 wherein said code is a bar code, said means being a bar code reading head.

46. The apparatus of claim 1 wherein means are provided for injecting cDNA and/or mRNA into said cell.

47. The apparatus of claim 46 wherein said means are located on an actuator.

48. An apparatus for conducting electrophysiological measurements on cells comprising a measuring head provided with at least two electrodes for impaling said cells of which at least one electrode is configured as a measuring electrode, and at least one perfusion conduit made as a perfusion inlet, wherein said electrodes and said at least one perfusion conduit are molded into a common support, said electrodes are arranged essentially symmetrical relative to a longitudinal axis of said support, and wherein at least one electrode has a straight section enclosing an acute angle α with said longitudinal axis of said support, and wherein said perfusion inlet is arranged essentially on a symmetry axis between said electrodes, and wherein said perfusion inlet has a first end opening, said perfusion inlet being arranged essentially parallel with said electrodes, and said first end opening being located above a lower end of said at least one measuring electrode.

49. An apparatus For conducting electrophysiological measurements on cells comprising a measuring head provided with at least one measuring electrode for impaling said cells with at least one reference electrode, with one first perfusion conduit made as a perfusion inlet, with a second perfusion conduit made as a perfusion outlet, wherein said at least one measuring electrode and said at least one reference electrode and said perfusion conduits are molded into a common support, said perfusion inlet has a first end opening and is arranged essentially parallel with said at least one measuring electrode, said first end opening being located above a lower end of said at least one measuring electrode, and said perfusion outlet has a second end opening being located above the first end opening.

50. An apparatus for conducting electrophysiological measurements on cells comprising a measuring head provided with at least two measuring electrodes for impaling said cells, at least two reference electrodes, a first perfusion conduit made as a perfusion inlet having a first end opening, a second perfusion conduit made as a perfusion outlet, said at least two measuring electrodes are molded into a common support, said at least two measuring electrodes are arranged in a first common plane and said at least two reference electrodes are arranged in a second common plane, said first and said second plane extend parallel to each other, and as viewed on said first plane, said perfusion inlet, is located in front of said first plane and said perfusion outlet is located behind said second plane, said perfusion inlet being arranged essentially parallel with said at least two measuring electrodes, said first end opening being located above a lower end of said at least two measuring electrodes.

51. An apparatus for conducting electrophysiological measurements on cells comprising a plurality of measuring heads arranged on an actuator, said measuring heads are provided with at least one electrode for impaling said cells, said at least one electrode is integrated into a support, wherein said measuring heads are adapted to be displaced individually relative to said actuator along said axis z directed towards said cells.

52. An apparatus for conducting electrophysiological measurements on cells with at least one measuring electrode for impaling said cells, with at least one reference electrode, with a first perfusion conduit made as a perfusion inlet having a first end opening for supplying perfusate to the cells, said perfusion inlet being arranged essentially parallel with said at least one electrode, said first end opening being located above a lower end of said at least one electrode, a second perfusion conduit made as a perfusion outlet having a second end opening for purging perfusate away from the cells, said second end opening being located above the first end opening, wherein said at least one measuring electrode is molded together with said at least one reference electrode and with said perfusion conduits into a common support of a measuring head.

53. An apparatus for conducting electrophysiological measurements on cells comprising a measuring head provided with at least one measuring electrode for impaling said cells, with at least one perfusion conduit made as a perfusion inlet having a first end opening, with at least one perfusion conduit made as a perfusion outlet having a second end opening being located above said first end opening, wherein said end openings are oriented along opposite directions, wherein said at least one measuring electrode is integrated into a support, said at least one perfusion inlet being arranged essentially parallel with said at least one measuring electrode, and said first end opening being located above a lower end of said at least one measuring electrode.

54. An apparatus for conducting electro-physiological measurements on cells comprising a measuring head provided with at least one measuring electrode for impaling said cells, with at least one perfusion conduit made as a perfusion inlet having a first end opening, wherein said at least one measuring electrode is integrated into a support, said at least one perfusion inlet being arranged essentially parallel with said at least one measuring electrode, and said first end opening being located above a lower end of said at least one measuring electrode, said apparatus further comprising a receptacle for said cells wherein said measuring head is arranged on an actuator, said actuator being adapted to be displaced along a coordinate system above said receptacle, wherein said actuator carries a plurality of measuring heads, wherein said measuring heads are adapted to be displaced individually relative to said actuator along said axis z directed towards said cell.

* * * * *

UNITED STATES PATENT AND TRADEMARK OFFICE
CERTIFICATE OF CORRECTION

PATENT NO. : 6,815,197 B2
DATED : November 9, 2004
INVENTOR(S) : Karl-Heinz Boven et al.

It is certified that error appears in the above-identified patent and that said Letters Patent is hereby corrected as shown below:

Column 2,
Line 57, "$\mu$pm" should read -- $\mu$m --;

Column 3,
Line 13, "con-trolled" should read -- controlled --;

Column 11,
Lines 40 and 42, "wherein least" should read -- wherein at least --.

Signed and Sealed this

Twenty-seventh Day of September, 2005

JON W. DUDAS
*Director of the United States Patent and Trademark Office*